US009919712B1

(12) United States Patent
Doyen et al.

(10) Patent No.: US 9,919,712 B1
(45) Date of Patent: Mar. 20, 2018

(54) CREW BIOMETRICS AND AIRCRAFT DATA ANALYSIS WITH REAL-TIME AND PROACTIVE ACTIONS

(71) Applicant: Rockwell Collins, Inc., Cedar Rapids, IA (US)

(72) Inventors: William G. Doyen, Annapolis, MD (US); Simon Critchley, Cheshire (GB); Patrick D. McCusker, Walker, IA (US); Talha S. Ansari, Marion, IA (US); John M. Connelly, Cedar Rapids, IA (US)

(73) Assignee: Rockwell Collins, Inc., Cedar Rapids, IA (US)

(*) Notice: Subject to any disclaimer, the term of this patent is extended or adjusted under 35 U.S.C. 154(b) by 219 days.

(21) Appl. No.: 14/937,591

(22) Filed: Nov. 10, 2015

Related U.S. Application Data

(63) Continuation-in-part of application No. 14/822,565, filed on Aug. 10, 2015, now Pat. No. 9,637,133.

(51) Int. Cl.
*G08B 23/00* (2006.01)
*B60W 40/08* (2012.01)

(52) U.S. Cl.
CPC ..... *B60W 40/08* (2013.01); *B60W 2040/0818* (2013.01)

(58) Field of Classification Search
CPC combination set(s) only.
See application file for complete search history.

(56) References Cited

U.S. PATENT DOCUMENTS 9,637,133 B1* 5/2017 McCusker ............ B60W 40/08
2016/0082838 A1* 3/2016 Melas ................. G06K 9/00845
340/575

* cited by examiner

*Primary Examiner* — Travis Hunnings
(74) *Attorney, Agent, or Firm* — Angel N. Gerdzhikov

(57) ABSTRACT

A system and method may monitor the biometric data of an operator in real time or near real time. Low cost electronic devices may monitor operator vital signs and biometric data allowing the system to determine stress levels, hydration levels, possible illness, body or blood chemical levels, incapacitation risks, and other biometric parameters of the operator, and proactively notify the operator, others aboard the vehicle, the vehicle control systems, or ground control to take responsive action. Industrial electronics may enable the system to monitor ambient workspace temperature, pressure, oxygen levels, and other environmental parameters, offering the system an additional second source of information to detect and address factors affecting the capacity of the operator. The system may further compare biometric and ambient parameters to archived operator, ambient, location, route, or vehicle performance data to determine and respond to long-term data patterns.

13 Claims, 8 Drawing Sheets

CREW BIOMETRICS AND AIRCRAFT DATA ANALYSIS WITH REAL-TIME AND PROACTIVE ACTIONS

CROSS-REFERENCE TO RELATED APPLICATIONS

The present application is a Continuation in Part and claims the benefit under 35 U.S.C. § 120 of U.S. patent application Ser. No. 14/822,565 filed Aug. 10, 2015 entitled "Operator Capacity Monitor and Engagement of Emergency Action System and Method" which is incorporated by reference in its entirety.

FIELD OF THE INVENTIVE CONCEPTS

Embodiments of the inventive concepts disclosed herein relate generally to monitoring a capacity of an operator of a vehicle. More particularly, embodiments of the inventive concepts disclosed herein relate to a system and related method for biometric monitoring of an operator as well as monitoring of an environment in which the operator is physically located and execution of a responsive action should the monitoring reveal an abnormality.

BACKGROUND

In single operator vehicles, early detection of operator incapacitation may be one method to reduce accidents. Some examples of single operator vehicles may include a small business aircraft as well as a current military fighter aircraft and a commuter train. Incapacitation of the single operator may lead to dire consequences.

In aviation, a number of catastrophic or near catastrophic events including pilot suicide, and errors due to pilot fatigue such as inadvertent pilot sleep, overflying a destination, and/or landing at the wrong airport can occur. These situations may pose serious potential consequences to the safety of the passengers, crew and those on the ground.

Traditional operator monitoring solutions may employ a pulse oximeter system physically temporarily attached to the finger of the single operator to measure blood oxygen saturation. During high workload where the operator may need the use of the finger, these devices are problematic as they interfere with the operator's ability to manipulate controls. These traditional devices may also be limited to measuring one parameter of interest (oxygen saturation) which can detect oxygen deprivation caused by, for example, a slow depressurization event in an aircraft. However, theses traditional devices are unable to detect additional sources of threats to the cognizance and consciousness of the single operator.

SUMMARY

In one aspect, embodiments of the inventive concepts disclosed herein are directed to a method for monitoring a capacity of an operator of a vehicle. The method may comprise accessing an acceptable range for an operator biometric parameter of the operator. The method may periodically receive the operator biometric parameter from an operator biometric monitor, comparing the received operator biometric parameter with the acceptable range.

The method may send a notification to the operator via a warning device if a result of the comparing includes an operator biometric parameter outside of the acceptable range. If the operator does not respond or intervene within a variable delay, the method may execute a response action if a result of the comparing includes an operator biometric parameter outside of the acceptable range. The response action may include 1) sending a notification to a co-pilot or crewperson of the vehicle, 2) adjusting a workspace ambient parameter of the vehicle, 3) activating an autopilot system of the vehicle, and 4) sending a notification offboard the vehicle.

In a further aspect, embodiments of the inventive concepts disclosed herein are directed to a method further including discontinuing the response action based on the receipt of an intervention from the operator during the variable delay.

In a further aspect, embodiments of the inventive concepts disclosed herein are directed to a method wherein the operator biometric parameter further includes a pulse rate, a respiration rate, a skin temperature, an activity level, a perspiration level, a voice stress level, a blood chemical level, and a breath chemical level, and the operator workspace ambient parameter further includes an air temperature, a motion level, an air pressure, a humidity level, a light level, a volume level, and an air chemical level.

In a further aspect, embodiments of the inventive concepts disclosed here in are directed to a method wherein sending a notification to the operator via a warning device of the vehicle further includes sending an auditory notification via an audio warning device, displaying a visual or textual notification to the operator via an operational display, and sending a tactile or vibratory modification to the operator via a physical warning device.

In a further aspect, embodiments of the inventive concepts disclosed herein are directed to a method wherein the physical warning device further includes the operator biometric monitor.

In a further aspect, embodiments of the inventive concepts disclosed herein are directed to a method further including acquiring an operator specific detail, acquiring an operational status of the vehicle, and adjusting the acceptable range based on the received operator specific detail and the operational status of the vehicle.

In a further aspect, embodiments of the inventive concepts disclosed herein are directed to a method wherein acquiring an operator specific detail further includes acquiring the operator specific detail from the data connection with an operator biometric monitor, an input from the operator, and a memory.

In a further aspect, embodiments of the inventive concepts disclosed herein are directed to a method further including establishing a data connection with a workspace ambient monitor configured for measuring an operator workspace ambient parameter, periodically receiving the operator workspace ambient parameter from the workspace ambient monitor, determining a first target data pattern by comparing the received operator workspace ambient parameter with the received operator biometric parameter, sending a notification to the operator via the warning device if a first target data pattern is determined, and executing a second response action via the warning device if a first target data pattern is determined, the second response action to be executed after a variable delay and including 1) sending a further or escalated notification to the operator; 2) sending a notification to a co-pilot or crewmember of the vehicle, 3) adjusting the operator workspace ambient parameter, 4) engaging the control system of the vehicle, and 4) sending a notification offboard the vehicle.

In a further aspect, embodiments of the inventive concepts disclosed herein are directed to a method further including discontinuing the response action based on the receipt of an intervention from the operator during the variable delay.

In a further aspect, embodiments of the inventive concepts disclosed herein are directed to a method further including determining a second target data pattern by comparing one or more of the received operator biometric parameter, the received operator workspace ambient parameter, archived data associated with the operator, archived data associated with the operator workspace ambient parameter, archived data associated with a location of the vehicle, and data associated with the performance of the vehicle.

In a further aspect, embodiments of the inventive concepts disclosed herein are directed to a method wherein determining the second target data pattern further includes establishing a data connection to an offboard processor, the offboard processor operatively coupled to an offboard memory configured to store one or more of the archived data associated with the operator, the archived data associated with the operator workspace ambient parameter, the archived data associated with a location of the vehicle, and the data associated with the performance of the vehicle.

In a further aspect, embodiments of the inventive concepts disclosed herein are directed to a method wherein the determining the second target data pattern may further include forwarding one or more of the received operator biometric parameter and the received operator workspace ambient parameter to the offboard processor via the data connection.

In a further aspect, embodiments of the inventive concepts disclosed herein are directed to a method wherein the determining the second target data pattern may further include comparing one or more of the received operator biometric parameter, the received operator workspace ambient parameter, archived data associated with the operator, archived data associated with the operator workspace ambient parameter, archived data associated with a location of the vehicle, and data associated with the performance of the vehicle via the offboard processor.

In a further aspect, embodiments of the inventive concepts disclosed herein are directed to a system for monitoring a capacity of an operator. The system may comprise a processor, a memory operatively connected with the processor, the memory storing non-transitory computer readable program code for monitoring the capacity of an operator of a vehicle, the computer readable program code comprising instructions which, when executed by the processor, cause the processor to perform and direct a plurality of steps including accessing an acceptable range for an operator biometric parameter of the operator. The system may periodically receive the operator biometric parameter via an operator biometric monitor and compare the received operator biometric parameter with the acceptable range. Should the comparison reveal an operator biometric parameter outside of the acceptable range, the system may send a first notification to the operator via a warning device. Should the operator not respond or intervene within a variable delay, the system may execute a first response action via the warning device. The response action may include 1) sending a subsequent or escalated notification to the operator; 2) sending a notification to a co-pilot or crewmember of the vehicle, 3) adjusting an operator workspace ambient parameter of the vehicle, 4) engaging an autopilot system of the vehicle, and 4) sending a notification offboard the vehicle.

In a further aspect, embodiments of the inventive concepts disclosed herein are directed to a system wherein the first processor is housed within any of a battery powered portable electronic device, a battery powered electronic flight bag, and an aircraft powered and certified electronic flight bag.

In a further aspect, embodiments of the inventive concepts disclosed herein are directed to a system wherein the processor is further configured for receiving an operator workspace ambient parameter from a workspace ambient monitor, determining a first target data pattern by comparing the operator workspace ambient parameter with the operator biometric parameter, sending a notification to the operator via a warning device of the vehicle if a first target data pattern is determined, executing a response action if a first target data pattern is determined or if the operator fails to respond to the initial notification, the response action including 1) sending a subsequent or escalated notification to the operator; 2) sending a notification to a co-pilot or crewmember of the vehicle, 3) engaging a control system of the vehicle, and 4) sending a notification offboard the vehicle.

In a further aspect, embodiments of the inventive concepts disclosed herein are directed to a system wherein the workspace ambient monitor further includes a portable battery powered monitor configured to be carried by the operator and a sensor installed in the workspace and receiving power from a vehicle power supply.

In a further aspect, embodiments of the inventive concepts disclosed herein are directed to a system wherein the operator biometric monitor further includes a monitor worn on a wrist of the operator, a monitor worn on a leg of the operator, a monitor worn on an extremity of the operator, a monitor proximal to a skin of the operator, and a monitor attached to a torso of the operator, and the operator biometric parameter further includes a pulse rate, a respiration rate, a skin temperature, an activity level, a perspiration level, a voice stress level, a blood chemical level, and a breath chemical level.

In a further aspect, embodiments of the inventive concepts disclosed herein are directed to a system wherein the processor is further configured for acquiring an operator specific detail via the operator biometric monitor, an input from the operator, or a memory; for acquiring an operational status of the vehicle; and for adjusting the acceptable range based on the received operator specific detail and the received operational status of the vehicle.

In a further aspect, embodiments of the inventive concepts disclosed herein are directed to a system wherein the processor is further configured for determining a second target data pattern by comparing one or more of the received operator biometric parameter, the received operator workspace ambient parameter, archived data associated with the operator, archived data associated with the operator workspace ambient parameter, archived data associated with a location of the vehicle, and data associated with the performance of the vehicle.

In a further aspect, embodiments of the inventive concepts disclosed herein are directed to a system further comprising a ground-based processor and a ground-based memory operatively connected to the ground-based processor and configured for storing one or more of the archived data associated with the operator, the archived data associated with the operator workspace ambient parameter, the archived data associated with a location of the vehicle, and the data associated with the performance of the vehicle.

In a further aspect, embodiments of the inventive concepts disclosed herein are directed to a system wherein the processor may be further configured for forwarding one or more of the received operator biometric parameter and the received operator workspace ambient parameter to the ground-based processor via the data connection.

In a further aspect, embodiments of the inventive concepts disclosed herein are directed to a system wherein the ground-based processor may be further configured for accessing the acceptable range of the operator biometric parameter, receiving the operator biometric parameter, comparing the received operator biometric parameter with the acceptable range, directing the warning device to send the first notification to the operator if the operator biometric parameter is outside the acceptable range, determining a response action to be executed via the ground-based processor if the operator biometric parameter is outside the acceptable range, the response action to be executed after a variable delay and including 1) directing the warning device to send a subsequent or escalated notification to the operator, 2) directing the warning device to send a notification to a co-pilot or crewmember aboard the vehicle, 3) directing a vehicle control system to adjust an operator workspace ambient parameter of the vehicle, and 4) activating an autopilot system of the vehicle.

In a further aspect, embodiments of the inventive concepts disclosed herein are directed to a system wherein the ground-based processor may be further configured for discontinuing the response action based on the receipt of an intervention from the operator during the variable delay.

In a further aspect, embodiments of the inventive concepts disclosed herein are directed to a system wherein the ground-based processor may be further configured for receiving the operator workspace ambient parameter; determining a first target data pattern by comparing the received operator biometric parameter and the received operator workspace ambient parameter; directing the warning device to send the notification to the operator if a first target data pattern is determined; determining a response action to be executed via the ground-based processor if the target data pattern is determined, the response action to be executed after a variable delay and including 1) directing the warning device to send a subsequent or escalated notification to the operator, 2) directing the warning device to send a notification to a co-pilot or crewmember aboard the vehicle, 3) directing a vehicle control system to adjust an operator workspace ambient parameter of the vehicle, and 4) activating an autopilot system of the vehicle; and discontinuing the response action based on the receipt of an intervention from the operator during the variable delay.

In a further aspect, embodiments of the inventive concepts disclosed herein are directed to a system wherein the ground-based processor may be further configured for determining a second target data pattern by comparing the received operator biometric parameter, the received operator workspace ambient parameter, archived data associated with the operator, archived data associated with the operator workspace ambient parameter, archived data associated with a location of the vehicle, and data associated with the performance of the vehicle; directing the warning device to send a notification to the operator if a second target data pattern is determined; determining a response action to be executed via the ground-based processor if the second target data pattern is determined, the response action to be executed after a variable delay and including 1) directing the warning device to send a subsequent or escalated notification to the operator, 2) directing the warning device to send a notification to a co-pilot or crewmember aboard the vehicle, 3) directing a vehicle control system to adjust an operator workspace ambient parameter of the vehicle, and 4) activating an autopilot system of the vehicle; and discontinuing the response action based on the receipt of an intervention from the operator during the variable delay.

It is to be understood that both the foregoing general description and the following detailed description are exemplary and explanatory only and are not necessarily restrictive of the inventive concepts disclosed herein as claimed. The accompanying drawings, which are incorporated in and constitute a part of the specification, illustrate embodiments of the inventive concepts disclosed herein and together with the general description, serve to explain the principles of the inventive concepts.

BRIEF DESCRIPTION OF THE DRAWINGS

The numerous advantages of the inventive concepts disclosed herein may be better understood by those skilled in the art by reference to the accompanying figures in which.

DETAILED DESCRIPTION

Figure 1:
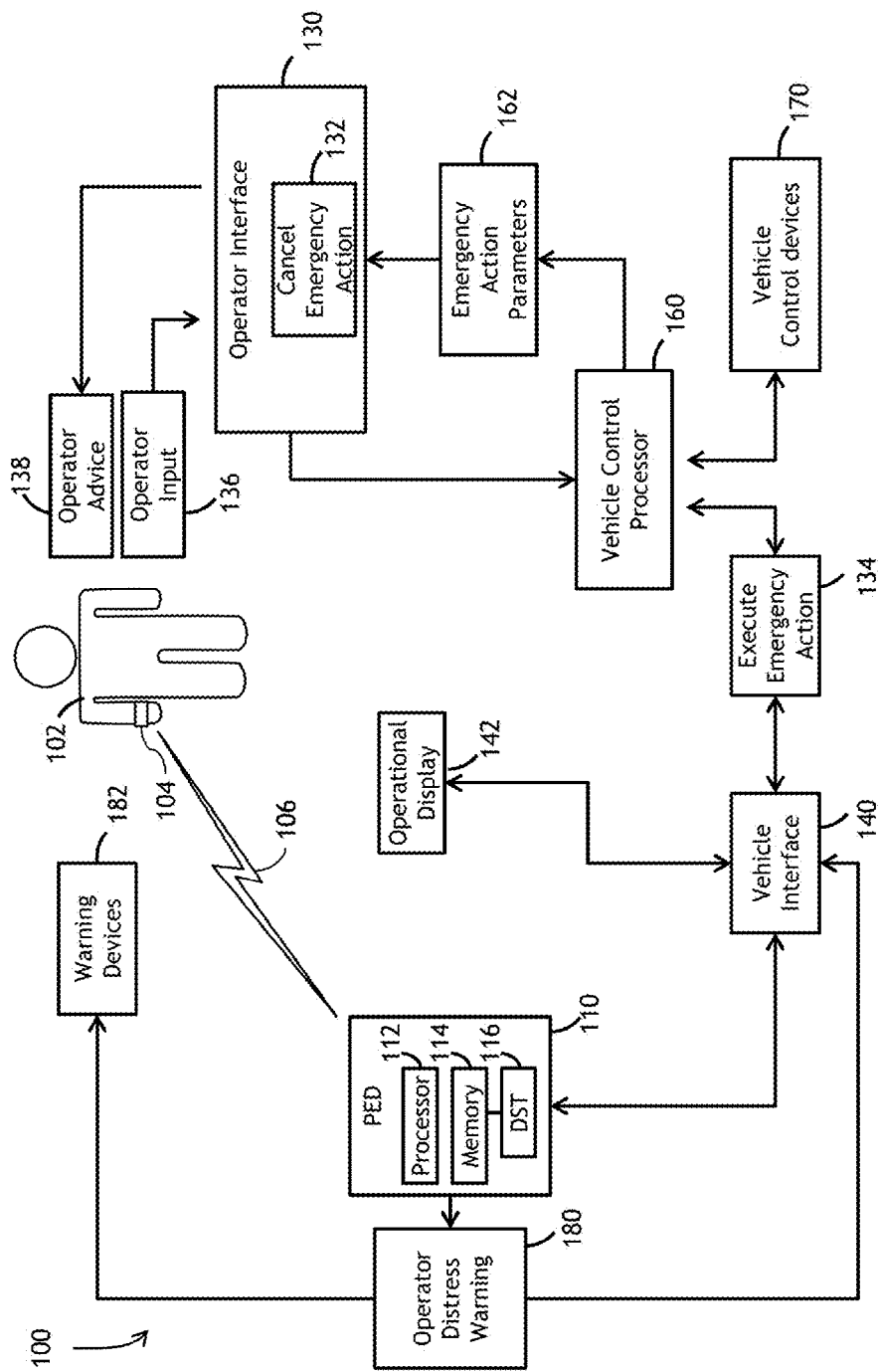
FIG. 1 is a diagram of a system for capacity monitoring of an operator in accordance with an embodiment of the inventive concepts disclosed herein.

Reference will now be made in detail to the presently preferred embodiments of the inventive concepts disclosed herein, examples of which are illustrated in the accompanying drawings.

The following description presents certain exemplary embodiments of the inventive concepts disclosed herein. However, the inventive concepts disclosed herein may be embodied in a multitude of different ways as defined and covered by the claims. In this description, reference is made to the drawings wherein like parts are designated with like numerals throughout.

Embodiments of the inventive concepts disclosed herein are directed to a system and related method for monitoring an operator of a vehicle for signs of incapacity. The system may employ low-cost, consumer electronics to monitor operator vital signs allowing the system to determine when the operator is active and normally operating the vehicle, operating the vehicle under a high workload, and/or has become inactive (potentially incapacitated). The system may also employ low-cost, industrial electronics to monitor ambient workspace temperature, pressure, and oxygen levels and may offer the system a second redundant source of information to detect ambient factors affecting the capacity of the operator. Should operator capacity be in question, the system may warn the operator and take an appropriate safety based action including application of a vehicle control system and eventually assuming control of the vehicle.

In addition, the systems herein may transmit from a vehicle and perform detailed analysis upon, a near continuous stream of data relating to the biometrics of the operator (s). Coupled with additional data streams identifying a level of automation in use at the time of biometric data capture, the detailed analysis may provide insight into the operator's physical status. Also from this detailed analysis, the systems disclosed herein may determine an anomaly within the data stream and act upon the anomaly in the appropriate manner.

Reference Chart

| Ref. No. | Description |
|---|---|
| 100 | System for Vehicle Operator |
| 102 | Operator |
| 104 | Operator Physical Monitor |
| 106 | Wireless Monitor Connection |
| 110 | Portable Electronic Device |
| 112 | Processor |
| 114 | Memory |
| 116 | Decision Support Tools |
| 120 | Workspace Ambient Sensor |
| 122 | Wireless Ambient Sensor Connection |
| 130 | Operator Interface |
| 132 | Cancel Emergency Action |
| 134 | Execute Emergency Action |
| 136 | Operator Input |
| 138 | Operator Advice |
| 140 | Vehicle Interface |
| 142 | Operational Display |
| 160 | Vehicle Control Processor |
| 162 | Emergency Action Parameters |
| 170 | Vehicle Control Devices |
| 180 | Operator Distress Warning |
| 182 | Warning Devices |
| 200 | Aircraft Embodiment |
| 202 | Pilot |
| 230 | Up Front Control |
| 236 | Pilot Input |
| 238 | Pilot Advice |
| 240 | Avionics Interface |
| 242 | Horizontal/Vertical Situation Display |
| 244 | Engine-Indicating and Crew-Alerting System (EICAS) |
| 246 | External Ambient Sensor |
| 260 | Autopilot |
| 272 | Flight Controls |
| 274 | Auto throttles |
| 276 | Speed brakes |
| 278 | Wheel Brakes |
| 280 | Pilot Distress Warning |
| 282 | Audio Warning Device |
| 284 | Video Warning Device |
| 286 | Physical Warning Device |
| 300 | Certified Embodiment |
| 310 | Class Three Electronic Flight Bag (EFB) |
| 320 | Certified Sensors |
| 322 | Certified Sensor Connection |
| 360 | Datalink |
| 400 | Flowchart |
| 402 | Receive Parameter Acceptable Range |
| 404 | Connect with 1) Operator monitor 2) ambient sensor |
| 406 | Receive Specific Operator Details |
| 408 | Adjust Parameter Acceptable Range |
| 410 | Monitor Operator and Ambient Parameters |
| 412 | Parameters Adjusted Range |
| 414 | Send Pilot Distress Warning |
| 416 | Workstation Parameters Within Adjusted Range |
| 418 | Begin Countdown |
| 420 | Notify Operator |
| 422 | Operator Intervention |
| 424 | Execute Emergency Action |

-continued

Reference Chart

| Ref. No. | Description |
|---|---|
| 500 | Biometric Embodiment |
| 502 | Co-Pilot/Crewmember |
| 504 | Biometric Sensor |
| 506 | Wireless Monitor Connection |
| 600 | Ground-based Biometric Embodiment |
| 602 | Vehicle |
| 610 | Ground-based Processor |
| 612 | Air Traffic Control/Ground Control |
| 614 | ATC Interface |
| 616 | Ground-based Relay Tower |
| 618 | Ground-based Memory |
| 620 | Archived Pilot/Operator Data |
| 622 | Archived Ambient Parameter Data |
| 624 | Archived Location/Route Data |
| 626 | Archived Vehicle Performance Data |
| 700 | Flowchart (biometric embodiment) |
| 702 | Access biometric/ambient parameters |
| 704 | Receive specific operator details |
| 706 | Adjust parameter acceptable range |
| 708 | Receive/monitor biometric/ambient parameters |
| 710 | Detect parameter outside range/target data pattern |
| 712 | Start variable delay |
| 714 | Notify operator based on parameter/TDP |
| 716 | Determine whether operator intervention occurred during delay |
| 718 | Execute response action based on parameter/TDP |
| 720 | Compare biometric/ambient parameters to archived data |
| 800 | Flowchart (ground-based embodiment) |
| 802 | Access biometric/ambient parameters via ground-based processor |
| 804 | Receive specific operator details via ground-based processor |
| 806 | Adjust parameter acceptable range via ground-based processor |
| 808 | Receive/monitor biometric/ambient parameters via ground-based processor |
| 810 | Detect parameter outside range/target data pattern via ground-based processor |
| 812 | Start variable delay |
| 814 | Notify operator based on parameter/TDP via ground-based processor |
| 816 | Determine whether operator intervention occurred during delay |
| 818 | Execute response based on parameter/TDP via ground-based processor |
| 820 | Compare biometric/ambient parameters to archived data via ground-based processor |

As described herein, one exemplary embodiment may include a description of an operator as a pilot and the vehicle as an aircraft. This aircraft embodiment may be one embodiment chosen for exemplary purposes and operates to describe the specifics of the inventive concepts herein. It is contemplated a wide variety of vehicles and operators (e.g., automobiles, trucks, bus, trains, single piloted and multi-piloted vehicles, helicopters and any situation where an incapacity of a single human may cause adverse consequences) may find direct benefit from the inventive concepts disclosed herein.

Referring to FIG. 1, a diagram of a system 100 for capacity monitoring of an operator in accordance with an embodiment of the inventive concepts disclosed herein is shown. The system 100 may include a portable electronic device (PED) 110 configured with a processor 112, a memory 114, and decision support tools associated with the memory 114. An operator 102 may be fitted with an operator physical monitor 104 configured for measuring a physical parameter of the operator 102 and transmitting data indicative of the measured physical parameter to the PED 110 via a wireless monitor connection 106.

In proximity with the operator 102, warning devices 182 may operate to provide a warning to the operator 102, an operator input 136 may receive an input from the operator 102 while an operator advice 138 may be configured to transmit information to the operator 102. An operator interface 130 may function to receive the input from the operator 102 and transmit to a vehicle control processor 160. Also, the operator interface 130 may function to receive emergency action parameters 162 and communicate the emergency action parameters 162 to the operator 102. In addition, the operator interface 130 may function as a medium for which the operator 102 may intervene to cancel the emergency action 132 via an operator input 136.

An operational display 142 may be a display screen configured for providing the operator 102 information relating to the status of the vehicle. A vehicle interface 140 may provide the operational display 142 with vehicle related information as well as receive an additional input from the operator 102.

The PED 110 may provide the housing and power source for the processor 112 to determine whether and when to issue an operator distress warning 180. The operator distress warning 180 may be transmitted to the vehicle interface 140 for transmission to the operational display 142 and to the warning devices 182 to provide the warning to the operator 102.

Prior to an operational state, the PED 110 may receive and store within the memory 114 an acceptable range for the operator physical parameters. The acceptable range may include a maximum and minimum value for each of the operator physical parameters historically applicable to a normal operator in operation of the vehicle. For example, a normal pulse rate, normal perspiration rate for specific phases of operation (e.g., normal workload, high workload) may be specific operator physical parameters monitored by the system 100.

In one embodiment, a pilot may wear the operator physical monitor 104 on the wrist of the hand most often involved in operating the aircraft and avionics systems. For example, a pilot sitting in the left seat may commonly use the right hand to manipulate the throttles, cursor control devices, switches, and knobs in the aisle stand, glare shield control panel, and overhead panel. Conversely, a pilot sitting in the right seat may commonly use the left hand to access these same avionics and aircraft controls and interfaces.

In additional embodiments, the operator physical monitor 104 may be worn on a leg of the operator 102, or worn on an extremity of the operator 102 (e.g., around a finger similar to a ring), a monitor proximal to a skin of the operator 102 (e.g., as an adhesive patch), and a monitor attached to a torso of the operator 102 (e.g., elastically attached around the chest).

In operation, the PED 110 may periodically receive and store to the memory 114 updated measured physical parameters of the operator 102 from the operator physical monitor 104 and compare the currently received measured physical parameters of the operator 102 to those stored in the memory 114. The periodic reception may be commanded by the PED 110 via a signal sent from the PED 110 to the operator physical monitor 104 commanding a response by the operator physical monitor 104 to transmit the measured physical parameters to the PED 110.

In embodiments, the physical parameters of the operator 102 may include a pulse rate, a respiration rate, a skin temperature, an activity level, and a perspiration level. For example, given an acceptable pulse rate range of 60 beats per minute to 120 beats per minute, the processor 112 may compare the received physical parameters of the operator 102 to this acceptable range. Should the current received pulse rate be outside of this range, the processor 112 may determine an operator distress warning 180 and sent the operator distress warning 180 to the warning devices 182 and the vehicle interface 140.

In an additional example, the PED 110 may be a Class 1 or Class 2 Electronic Flight Bag (EFB) configured to host a specific application within the memory 114 able to capture the vital signs measured by the operator physical monitor 104 worn by the operator 102. Preferably, a wrist-worn operator physical monitor 104 may function to measure the physical parameters and activity (motion) level of the operator 102, but additional types of activity monitors are contemplated within the scope of the inventive concepts disclosed herein.

The Decision Support Tools (DST) 116 stored within the memory 114 and accessible by the processor 112 may include additional sources of determination of the presence of an operator distress and incapacity. Additionally, the DST 116 may include additional economic motivation for the operator 102 to bring the PED 110 onboard the vehicle. For example, a safety management team or an insurance carrier may operate to encourage each operator 102 to only operate the vehicle with the PED 110 in operation and continuously monitoring the capacity of the operator 102. Integration of the system 100 operator capacity monitoring with these additional DST 116 may enable these tools to tailor their operations in appropriate ways based upon specific operator stress.

For example, a single operator 102 of a tour bus may experience an increased pulse rate coupled with an increased movement of one or both of the hands during driving through the mountains. The increased workload may indicate to the system 100 the single operator 102 may be experiencing stress and require an operator distress warning 180. Here, the tour bus driver DST 116 may differ from those DST 116 used to monitor the single operator 102 of the locomotive (e.g., hand motion, accelerometer readings).

In operation, the system 100 may measure heart rate, body temperature, perspiration levels, and motion (using accelerometers), and compare the stored parameters with the measured parameters to determine:

1) Periods of high workload: for example, an increased heart rate, increased body temperature, increased perspiration, and increased motion of the commonly used hand;

2) Periods of inactivity (possibly indicating operator inattentiveness and/or sleepiness): for example, a decreased heart rate, decreased body temperature, decreased perspiration, and decreased motion of the commonly used hand; and 3) Oxygen deprivation: for example, an increased heart-rate coupled with decreased motion (and possibly slow, uncoordinated, or chaotic motion) of the commonly used hand.

The operator physical monitor 104 may allow the system 100 detection of at least three conditions which may affect the continued safe operation of the vehicle: 1) stress caused by high workloads; 2) loss of attention caused by low workloads; and 3) oxygen deprivation caused by a slow depressurization event that has gone undetected by other means.

In embodiments, the system 100 may operate to provide the operator distress warning 180 for at least three exemplary conditions:

Response 1)

During periods of high work load, the PED 110 may provide suggestions for further operator action; this may reduce workload and may help to break the operator 102 out of the a possible tunnel vision scenario that may occur during high stress situations. The operator physical monitor 104 may measure and transmit an increase pulse rate and increased perspiration rate. One possible suggestion for further action may be to "slow down" displayed on the operational display 142 for this high workload scenario.

Response 2)

If the operator 102 has become inattentive (or even fallen asleep), (e.g., the operator physical monitor 104 is measuring a reduced pulse rate coupled with a reduced respiration rate) the system 100 may issue an escalating series of operator distress warnings 180 (first a textual warning on the operational display 142 (e.g., Warning—confirm you are awake?); then text and audio tones via the warning devices 182; then text and speech via the warning devices 182) to get the attention of the operator 102 and to request an acknowledgement Response 3)

The system 100 may begin with an escalating series of alerts (e.g., notification, cautions, and warnings) via the operational display 142 and the warning devices 182 followed by a delayed automated execution of an emergency action 134 via an application of the vehicle control devices 170. The emergency action 134 may include such actions as a reduction of a power source of the vehicle to idle, an application of a braking device associated with a wheeled vehicle, and application of an emergency descent to a safe altitude where the vehicle may be an aircraft.

For example, emergency action parameters 162 may include an application of a braking device such as a wheel brake on a semi-truck, a normal descent to a minimum safe altitude in the case of an incapacitated operator 102, an entry into a holding pattern, a transmission of an emergency signal, and an emergency descent profile in the case of a rapid depressurization event.

Should the operator 102 desire the system 100 to refrain from automated execution of the emergency action 134, the operator 102 may cancel the emergency action 132 at any time with the cancel emergency action 132 via operator interface 130.

Figure 2:
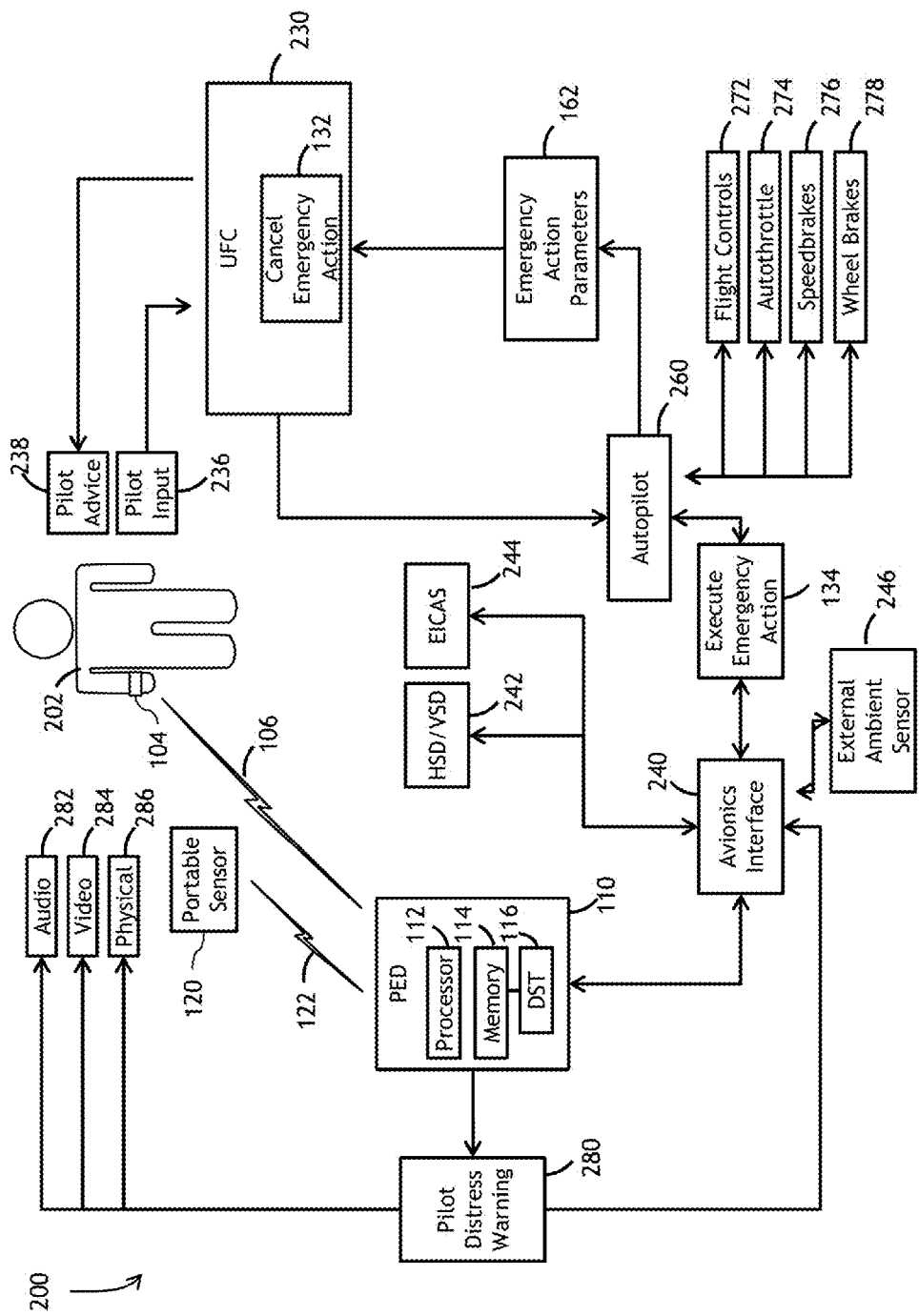
FIG. 2 is a diagram of a system for capacity monitoring of a pilot operator in accordance with an embodiment of the inventive concepts disclosed herein.

Referring to FIG. 2, a diagram of a system 200 for capacity monitoring of a pilot operator in accordance with an embodiment of the inventive concepts disclosed herein is shown. An aircraft embodiment system 200 sited onboard an aircraft may operate with similar function as the system 100.

The system 200 may include the PED 110 configured to receive the wireless signal 106 from the operator physical monitor 104 in addition, the PED 110 may be further configured to receive a wireless signal 122 transmitted from a workspace ambient sensor 120. The workspace ambient sensor 120 may be configured for sensing an ambient parameter within the workspace occupied by the pilot 202. For example, the workspace ambient sensor 120 may operate to sense, inter alia, an air temperature, a pilot motion level, an air pressure, a humidity level, acceleration, and an oxygen level within the workspace (cockpit and within the pressure hull of the aircraft).

The workspace ambient sensor 120 may operate as a stand-alone device configured for portability with its own battery power source. Alternatively, the workspace ambient sensor 120 may be configured within the PED 110 and share a common power source with the PED 110. Also, the workspace ambient sensor 120 may be connectable to the PED 110 via a combination power and data cable connection. For example, a Universal Serial Bus (USB) data connection may enable the PED 110 to provide power to as well as receive data from the workspace ambient sensor 120.

Additionally, Embedded Display System (EDS) elements Horizontal/Vertical Situation Display 242 and Engine-Indicating and Crew-Alerting System (EICAS) 244 may operate not only as a traditional interface between the pilot 202 and the avionics interface 240, but also as an additional source of the pilot distress warning 280 presented to the pilot 202.

Further, the EDS elements may function as an additional source for early recognition of pilot incapacity. Should a phase of flight require frequent interaction between the pilot 202 and the HSD 242, and the PED 110 may detect zero interaction by the pilot 202, this indication may be an additional DST 116 for the PED 110 to issue the pilot distress warning 280.

An external ambient sensor 246 may operate to provide an additional DST 116 to the PED 110 to issue a pilot distress warning 280. The external ambient sensor 246 may operate to sense the environment external to the workspace (e.g., outside the pressure hull of an aircraft, outside the cab of a truck). Should a combination of sensors including the operator physical sensor 104 and the external ambient sensor 246 indicate a measurement outside the acceptable range, the PED 110 may operate to issue the pilot distress warning 280.

Flight controls 272 including ailerons, rudder and elevator may be positioned by the autopilot 260 as the autopilot may be actively controlling the aircraft. Also, the autothrottles 274 may function to provide a power setting to the engines, speedbrakes 276 may provide the autopilot with additional drag while wheel brakes 278 may provide stopping power while the aircraft is on a runway.

In embodiments, the system 200 may receive an input associated with a pilot specific detail from the operator physical monitor 104. Based on the operator specific detail, the system 200 may adjust the acceptable range of operator physical parameters for the specific pilot 202. For example, a pilot 202 who is an avid runner may maintain a resting pulse rate lower than a pilot 202 who may have an increased body mass index and is a smoker. In this manner, the system 200 may tailor the operation of the pilot distress warning 280 to the specific pilot 202. Further, the adjustment to the acceptable range may be an adjustment of zero for an average operator or pilot 202.

In addition, the aircraft embodiment system 200 may adjust the acceptable range of the operator physical parameters based on an operational phase of vehicle (e.g., a phase of flight). For example, an increase in heart rate and an increase in blood pressure may be anticipated in a high workload environment (e.g., weapons delivery, air combat, or severe turbulence). The aircraft embodiment system 200 may adjust the acceptable range based on this anticipated increase in the operator physical parameters.

Additional warning devices including an audio warning device 282, a video warning device 284, and a physical warning device 286, one or more of which may operate to provide the pilot 202 with the pilot distress warning 280 issued by the PED 110. For example, one physical warning device 286 may include a vibration device and/or a periodic motion device associated with the seat of the pilot 202. In addition, the operator physical monitor 104 may function to rouse a sleeping or semi-conscious pilot 202 via the physical warning device 286 via a vibratory or pulsed response. In further embodiments, the operator physical monitor 104 may operate as a warning device via a vibration, pulse, and/or electric shock within the operator warning device 104.

An upfront control 230 may operate as an interface between a pilot input 236 and a pilot advice 238 and the autopilot 260. Integration of the pilot input 236 into the upfront controls 230 may offer an immediate access to the system 200 for the pilot 202. Some upfront controls 230 may include a master warning and master caution as well as easy access to commonly used features such as autopilot 260 controls, communication tools, and approach mode settings.

The aircraft embodiment of system 200 may operate to provide increasing warnings to the pilot 202 via the warning systems 282-286 while attempting to bring the incapacitated pilot 202 back into the flying role. The system 200 may begin a variable delay before executing the emergency action 134. The delay may be directly proportional to the situation in which the aircraft is currently flying.

For example, if the aircraft is in straight and level flight at 42,000 feet Mean Seal Level (MSL), and the operator physical monitor 104 reveals a reduced pulse rate, the workspace ambient sensor 120 reveals a reduction in oxygen level in the cockpit, the external ambient sensor 246 reveals an actual altitude of 42,000 feet MSL, and the workspace ambient sensor 120 also reveals a reduction in temperature, the PED 110 may use the DST 116 to determine a loss of cabin pressure is occurring. In this situation, the PED 110 may issue the pilot distress warning 280 and, followed by a 15 second variable delay for operator intervention, execute an emergency descent to 10,000 feet MSL as the appropriate emergency action 132. Here the PED 110 may direct the autopilot 260 to reduce the autothrottles 274 to idle, extend the speedbrakes 276 to a maximum deflection, and adjust the flight controls 272 for a nose down profile of an emergency descent.

Conversely, should the aircraft be operating in a combat environment in a 45 degree dive delivering weapons with only seconds to ground impact, the variable delay may be reduced to an exemplary two seconds of inactivity and reduced physical parameters before the system 200 may execute the emergency action. Also here, the emergency action may be considerably different and may include a command to the autopilot 260 to roll to wings level, an increase in the autothrottles 274 to climb power, and a commanded nose up attitude to climb to 10,000 feet MSL and level flight. Once in level flight, the system 200 may continue to send warnings to the pilot 202 and send a distress signal offboard the aircraft to a command authority for assistance.

Embodiments of the system 200 may also be tailored to a desired Design Assurance Level (DAL). A low DAL system 200 may request the autopilot perform the appropriate emergency action. However, a high DAL automated system may operate to confirm the pilot 202 is incapacitated prior to starting the descent (e.g., issuing the pilot distress warning 280 and implementing a delay timer to give the pilot 202 an option to cancel the emergency action).

Figure 3:
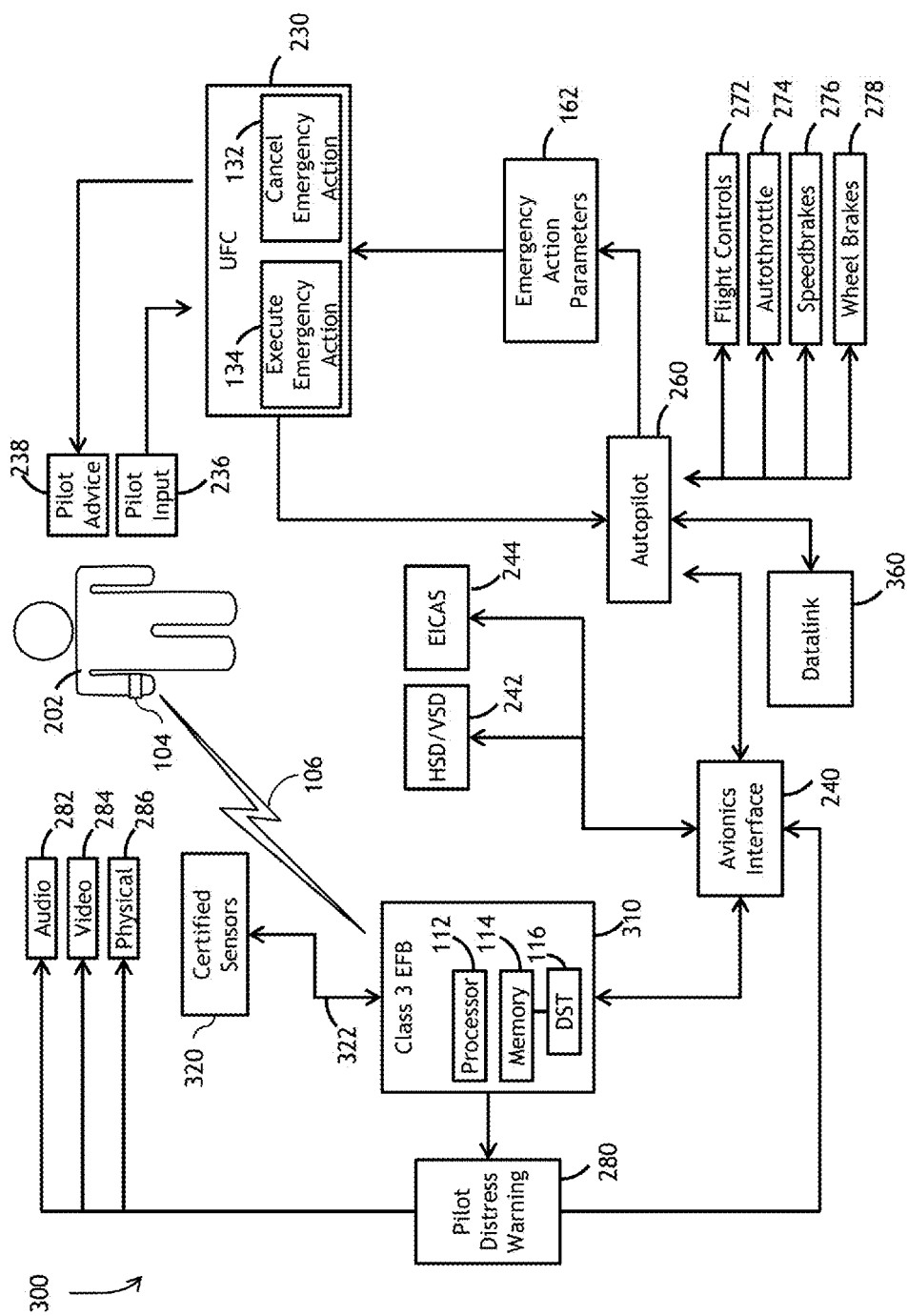
FIG. 3 is a diagram of a system for capacity monitoring of a pilot exemplary of an embodiment of the inventive concepts disclosed herein.

Referring to FIG. 3, a diagram of a certified system 300 for capacity monitoring of a pilot exemplary of an embodiment of the inventive concepts disclosed herein is shown. The certified system 300 may include a certified sensor 320 as the workspace ambient sensor suite. Certification of installed system onboard an aircraft may include additional steps to ensure operational applicability and compliance with rigorous performance standards. Certified sensors 320 may be coupled with a class three EFB 310 (also certified) via a certified sensor connection 322.

Also, the certified sensors 320 may be sited within the workspace in a variety of locations around the pilot 202. For example, a motion detector may be sited directly above the pilot 202 and configured for sensing the motion of the pilot 202 from above while one or more temperature and pressure sensors may be placed throughout the cockpit to aid in redundant operation of the certified system 300.

Within the certified system 300, additional high DAL system level functional safeguards may be in place within the certified avionics and autopilot 260 to ensure any disagreement between the class three EFB and the certified avionics results in a conservative action. For example, a high integrity certified avionics may perform a final analysis to determine if an emergency event is present and emergency action is warranted.

In an additional embodiment, the certified system 300 may operate in coordination with a datalink 360 to send and receive data offboard the aircraft. The datalink 360 may be directly associated with the autopilot 260 and configured to receive flight control inputs from a source offboard the aircraft. In this manner, should the pilot 202 become permanently incapacitated, an offboard control entity may operate the control surfaces of the aircraft and execute further emergency actions to ensure safety of the aircraft, passengers and cargo.

Figure 4:
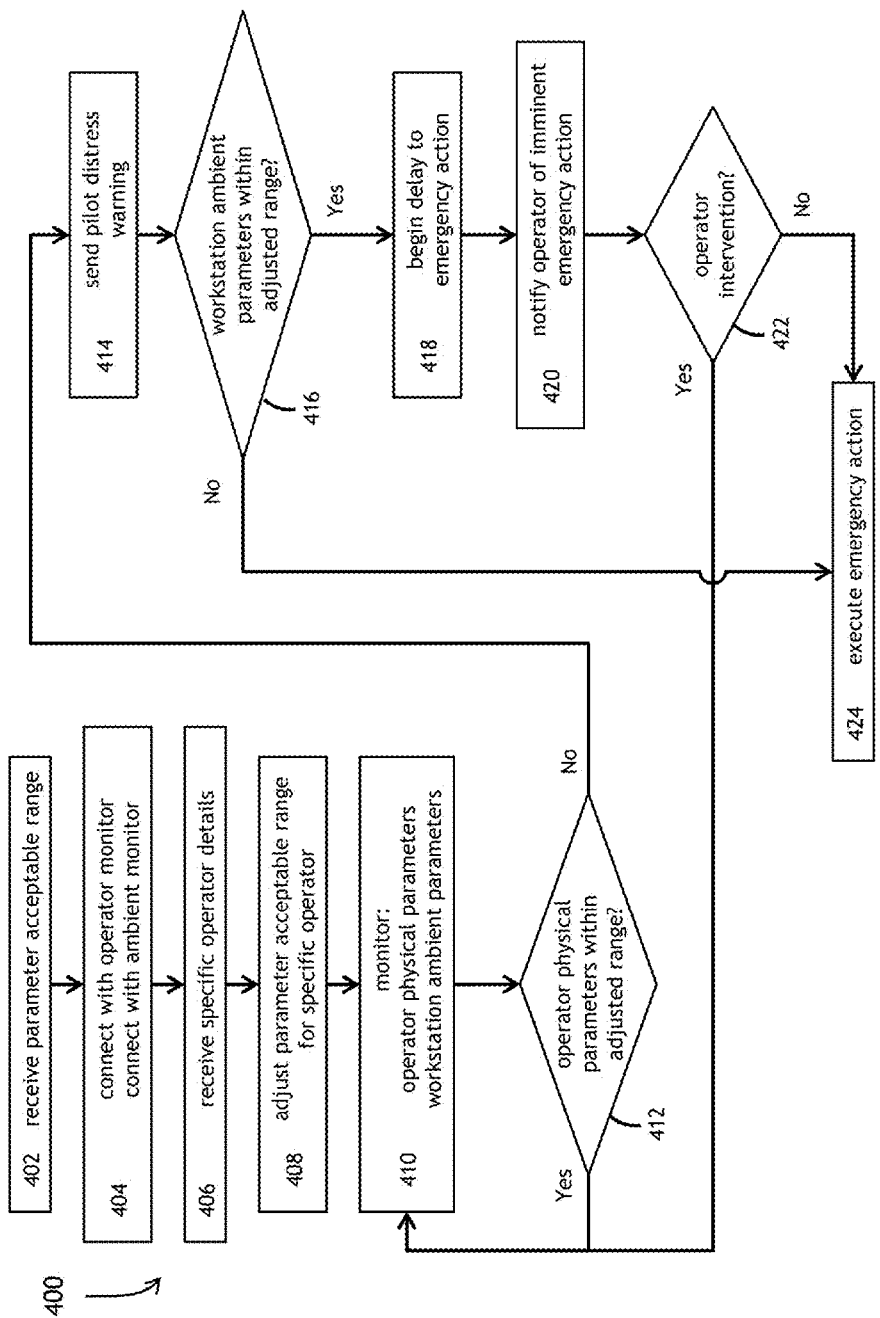
FIG. 4 is a flow diagram of a method for operator capacity monitoring exemplary of one embodiment of the inventive concepts disclosed herein.

Referring to FIG. 4, a flow diagram of a method 400 for operator capacity monitoring exemplary of one embodiment of the inventive concepts disclosed herein is shown. The method 400 for monitoring the capacity of an operator may include, at a step 402, receiving a parameter acceptable range, and at a step 404, connecting with an operator physical monitor as well as with a workspace ambient monitor. The method 400 may, at a step 406, receive specific operator details and, at a step 408, adjust the parameter acceptable range based on the received details associated with the operator.

The method may continue at a step 410 with monitoring each of the operator physical parameters and the workstation ambient parameters. At a step 412, the method may compare the received operator physical parameters with the stored and adjusted acceptable range and, if within the range, the method may continue to monitor at the step 410. However, if the operator physical parameters are outside the acceptable range, the method may, at a step 414, send a pilot distress warning to the operator. The method may, at a step 416, compare the workstation ambient parameters to the acceptable range. Should the result of the query 416 be negative, the method may flow (after a delay) directly to a step 424 of execution of an emergency action.

However, if the workspace parameters are within the acceptable range at the step 416, the method may, at a step 418, begin a delay countdown to the execution of the emergency action and, at a step 420, notify the operator of an imminent emergency action. The method may check for operator intervention at a step 422 and, receiving no operator intervention, the method may, at the step 424, execute the emergency action. Should the method receive an operator intervention, the method may return to the monitoring step 410.

Figure 5:
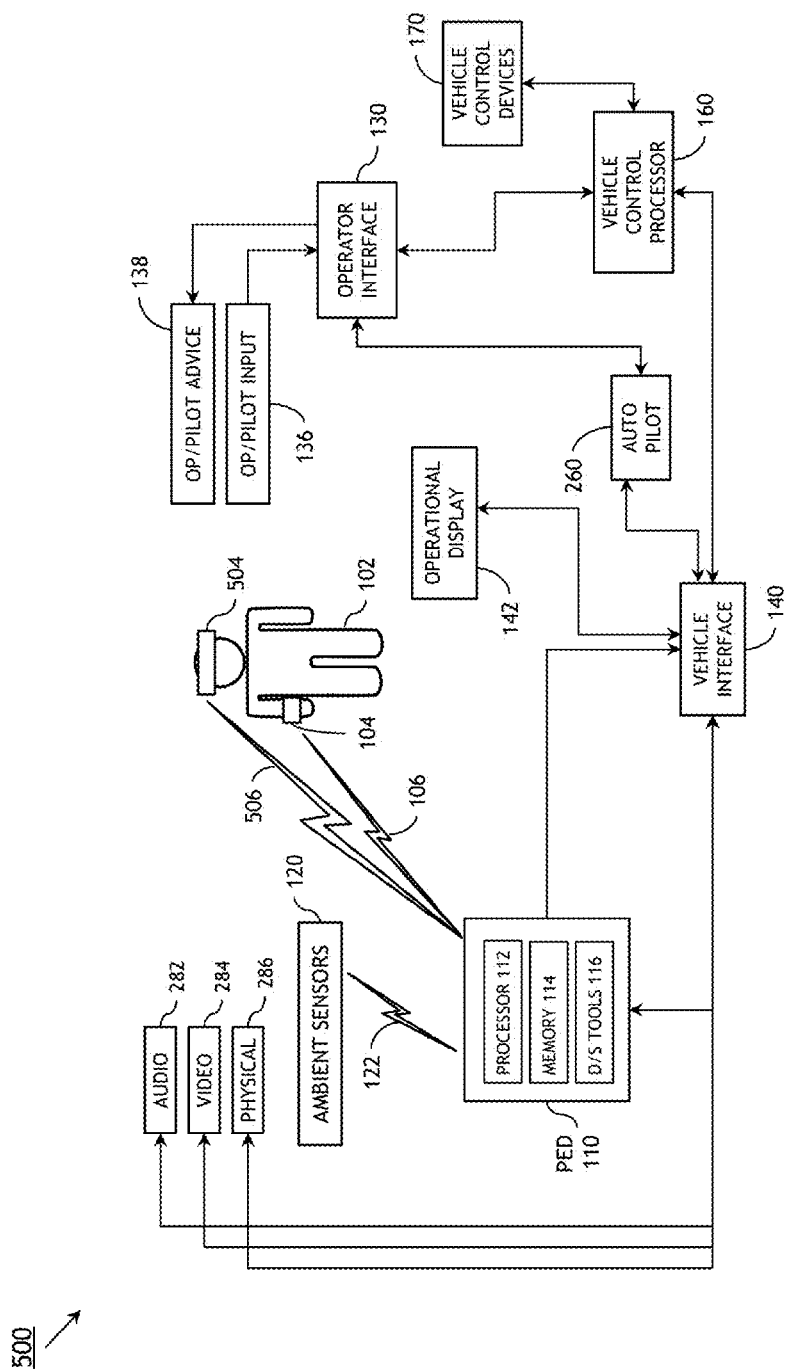
FIG. 5 is a diagram of a system for capacity monitoring of a pilot operator in accordance with an embodiment of the inventive concepts disclosed herein.

Referring to FIG. 5, a diagram of a system 500 for biometric monitoring of an operator 102 (ex.—pilot 202) in accordance with an embodiment of the inventive concepts disclosed herein is shown. A biometric embodiment system 500 situated aboard a vehicle may operate with similar function as the systems 100 and 200.

The system 500 may include the PED 110 configured to receive a wireless signal from an operator biometric monitor 504 in addition to the operator physical monitor 104. The operator biometric monitor 504 may be configured for sensing biometric parameters of the operator 102 and transmitting data indicative of the sensed biometric parameter to the PED 110 via a wireless monitor connection 506. In embodiments, the operator 102 may wear the operator biometric monitor 504 around a wrist, leg or other extremity, proximal to the skin, or attached to the torso in similar fashion to the operator physical monitor 104. The operator biometric monitor 504 may be positioned proximal to the mouth of the operator 102, or proximal to the bloodstream of the operator. In embodiments, the biometric parameters of the operator 102 may include voice stress levels detected via analysis of the speech of the operator or chemical levels (including oxygen, alcohol, or drugs) based on analysis of the exhalation, bloodstream, or other body chemicals of the operator.

Prior to an operational state, the PED 110 may access (ex.—determine, receive) acceptable ranges for the operator biometric parameters, storing the acceptable ranges to the memory 114. In operation, the PED 110 may periodically receive (via the wireless monitor connection 506) and store to the memory 114 updated sensed biometric parameters of the operator 102 from the operator biometric monitor 504, and compare currently received operator biometric parameters to those stored in the memory 114.

In operation, the system 500 may compare sensed biometric parameters with measured physical parameters (measured by the operator physical monitor 104) to identify target data patterns corresponding to conditions of the operator 102. For example, based on pulse rate, breathing rate or lack of speech detected by the operator biometric monitor 504, the system 500 may determine that the operator 102 is asleep or extremely tired. In one embodiment, the system 500 may analyze operator biometric parameters to raise or lower the confidence level of the detection of a condition based on operator physical parameters measured by an operator physical monitor 104 (i.e., high stress levels, inattentiveness, oxygen deprivation). For example, the operator biometric monitor 504 may include a blood chemistry sensor configured for detecting oxygen content in the bloodstream of the operator 102. If the operator biometric monitor 504 detects lower blood oxygen than normal, and the operator physical monitor 104 detects an increase in pulse rate and a decrease in body motion, the system 500 may more rapidly conclude that the operator 102 is experiencing oxygen deprivation, and may intervene at an earlier point to address the condition before the operator 102 is significantly impaired.

In operation, the system 500 may respond to a detected condition on the part of the operator 102 but determine that the detected condition does not require emergency intervention. The system 500 may address the detected condition by directly interacting with the operator 102, by notifying a co-pilot, crewmember, passenger, or other individual aboard the vehicle, or by indirectly intervening via a vehicle interface 140 of the vehicle. The system may generate an initial warning notification for the operator 102 and activate a delay within which the operator 102 may intervene or respond via, e.g., an operational display 142, operator interface 130, or warning device 282, 284, 286. The length of the delay may be pre-programmed according to business rules or mission parameters, and may depend on the particular target data pattern or anomalous parameter identified by the system 500. Should the operator 102 fail to respond or intervene within the allotted delay, the system 500 may take additional action to engage the attention of the operator 102 or address the identified anomaly, including the generation of additional, or escalating, notifications and warnings to the operator 102, notifications and warnings directed to other crewmembers or persons aboard the vehicle, or direct intervention with vehicle systems. For example, if the operator 102 appears to be tired or asleep, the system 500 may generate an audible warning via an audio warning device 282 (e.g., cockpit annunciator); display a visible or textual warning via a visual warning device 284 (e.g., a light panel) or an operational display 142 of the vehicle (e.g., display a message suggesting the operator request a cup of coffee); notify a flight attendant or crewmember outside the cockpit to check on the operator; generate a tactile or physical warning via a physical warning device 286 of the vehicle (e.g., raising the temperature of the operator's seat or gently vibrating the seat); adjust an ambient parameter of the vehicle via a vehicle control device 170 (e.g., raising the cockpit temperature by a few degrees or increasing cockpit lighting levels); engage a control system (e.g., an autopilot 260) of the vehicle; or send a notification offboard the vehicle (e.g., to ground control). In one embodiment, a physical warning device 286 of the vehicle may include the operator biometric monitor 504. For example, a wrist-mounted pulse monitor may be configured to gently vibrate when the system 500 determines that the operator 102 may be tired or inattentive.

In embodiments, the system 500 may receive an input associated with an operator specific detail from the operator biometric monitor 504. Based on the operator specific detail, the system 500 may adjust the acceptable range of operator biometric parameters for a given operator 102. In operation, the system 500 may compare received operator biometric parameters sensed by the operator biometric monitor 504 with received operator workspace ambient parameters sensed by a workspace ambient sensor 120. For example, the PED 110 may store to the memory 114 one or more target data patterns associated with concurrent values of an operator biometric parameter and an operator workspace ambient parameter. In the alternative, the processor 112 may detect target data patterns in the course of data analysis and store the target data patterns to memory 114. For example, the operator biometric monitor 504 may determine that the operator 102 is perspiring, whereby the system 500 may conclude that the operator is under elevated stress or possibly overheated. The system 500 may generate a notification for the operator 102 or respond (after a delay for operator intervention) by one or more of temporarily engaging the autopilot system 260 to automate some operator tasks (thus alleviating the burden on the operator 102), displaying an additional reminder to the operator via the operational display 142, or signaling the vehicle control processor 160 to slightly lower the cabin temperature. However, if the operator biometric monitor 504 indicates that the operator 102 is perspiring, and the workspace ambient sensor 120 indicates that cabin conditions (e.g., temperature and humidity) are such that this particular operator 102 (as defined by adjusted acceptable parameter ranges) should not be perspiring, the system 500 may recognize a target data pattern and infer that the operator 102 is running a fever or is otherwise ill, which may significantly affect operator performance. The system 500 may attempt to confirm or dispel this hypothesis by notifying the operator 102 or by referencing other workplace ambient parameters or operator biometric parameters. For example, the system 500 may analyze the body temperature of the operator 102 over the last few hours and conclude that the present condition of the operator 102 is anomalous. The system 500 may respond by sending a notification to the operator 102, or by notifying a co-pilot or other crewmember aboard the vehicle that the operator 102 may be ill, and suggesting responsive interventions to the co-pilot/crewmember (e.g., relieving the pilot, taking extra measures to avoid contagion if possible).

More than one target data pattern may be associated with a given set of operator biometric parameters and operator workspace ambient parameters. For example, the operator biometric monitor 504 may indicate no evidence that the operator 102 is perspiring, while the workplace ambient sensor 120 indicates cabin temperature and humidity such that this particular operator should be perspiring. The system 500 may interpret this data pattern by inferring that the operator 102 may be dehydrated and respond by sending a message to the operator (via the operational display 142) suggesting the operator request water. The system 500 may (after a delay for operator intervention) notify a crewmember aboard the vehicle and suggest that the crewmember provide the operator 102 with a bottle of water or other appropriate hydration.

In addition to analyzing operator biometric parameters and operator workspace ambient parameters in real time or near real time and responding in the short term to target data patterns, in one embodiment the system 500 compares received biometric and ambient parameters with archived data to determine longer-term target data patterns over time or variations from one or more baselines. For example, the PED 110 may store in the memory 114 operator biometric parameters and workspace ambient parameters associated with a particular operator 102 and collected throughout a flight by the operator biometric monitor 504 and the workspace ambient sensor 120. On a subsequent flight under similar conditions (e.g., along the same route, in a comparable vehicle, by the same operator at the same time of day) the system 500 may compare current operator biometric parameters and workspace ambient parameters with archived (ex.—previously collected) operator biometric parameters and workspace ambient parameters stored in the memory 114. In addition, the system 500 may detect medium-term and long-term target data patterns by cross-referencing biometric data and ambient data with other archived data stored in the memory 114, including (but not limited to) operator-specific data, location-specific data and route-specific data, and vehicle-specific performance data (e.g., fuel efficiency throughout a flight). The system 500 may develop long-term suggestions for responding to target data patterns by notifying one or more individuals or suggesting one or more business rules associated with the operation of a vehicle or fleet of vehicles, or the assignment of an operator or crew to a vehicle. For example, the system 500 may determine that a given operator 102 consistently (e.g., over the course of multiple flights or routes) presents increased voice stress levels when ambient sensors 120 indicate higher than normal cabin temperatures. The system 500 may respond by suggesting that any subsequent vehicles flown by the operator 102 adjust cabin temperatures accordingly to alleviate potential stress on the operator 102. The system 500 may further respond by suggesting to crewmembers serving with the operator 102 to check in on and converse with the operator 102 intermittently to determine if other factors (e.g., personal crisis, fatigue, chronic illness) may contribute to the elevated stress levels of the operator 102.

Furthermore, the system 500 may correlate a particular flight segment (e.g., a descent at the end of a transoceanic flight) or a particular time of day (e.g., late afternoon/early evening), with episodes of delayed response time, elevated stress levels, and below-average fuel efficiency throughout all operators and vehicles. The system 500 may attempt to infer explanations for these long-term target data patterns and suggest potential responsive measures based on training regimens, mission parameters, or business rules.

Figure 6:
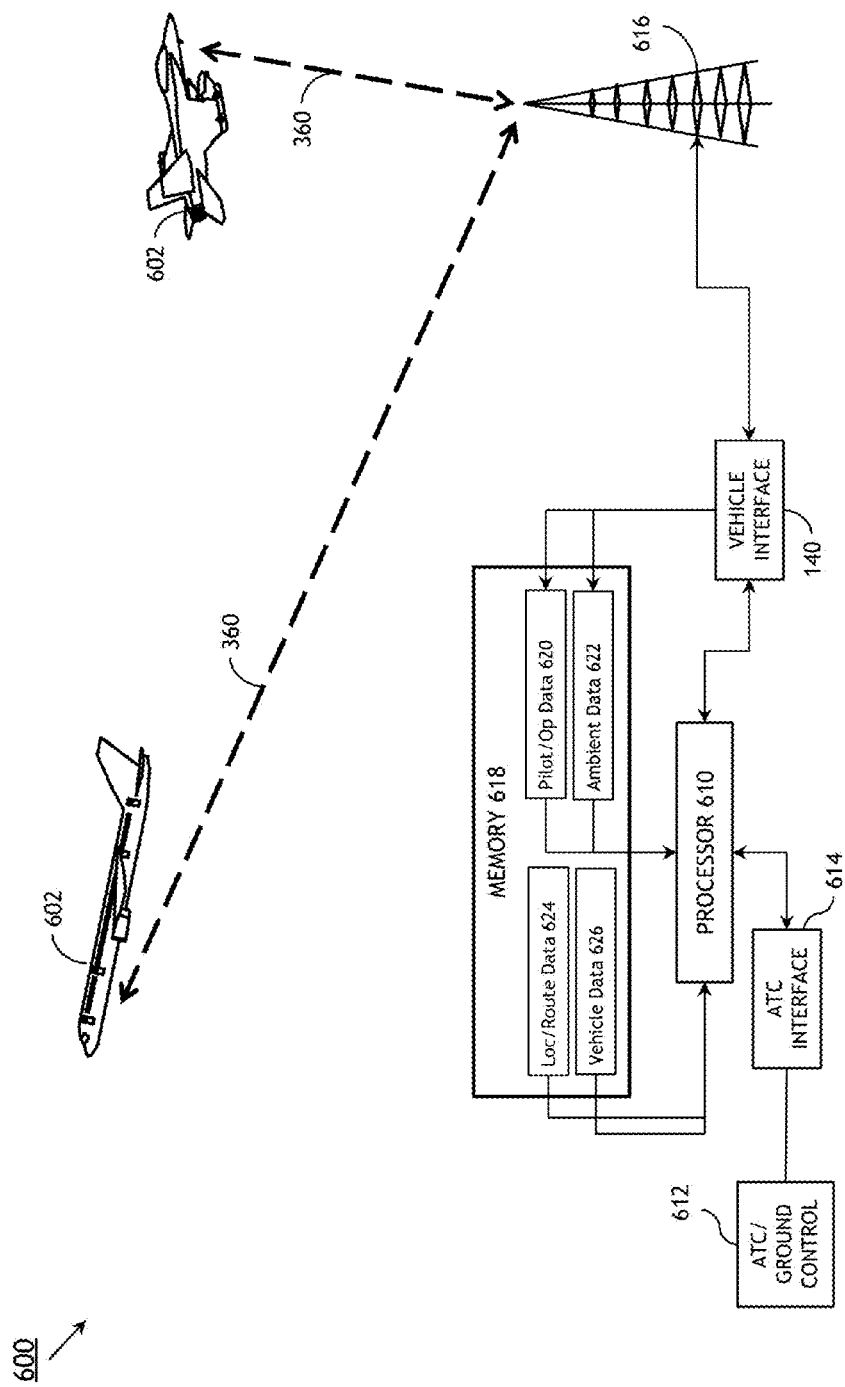
FIG. 6 is a diagram of a system for capacity monitoring of a pilot operator in accordance with an embodiment of the inventive concepts disclosed herein.

Referring to FIG. 6, a diagram of a system 600 for biometric monitoring of one or more operators (not shown) aboard one or more vehicles 602 in accordance with an embodiment of the inventive concepts disclosed herein is shown. A multi-vehicle biometric embodiment system 600 may operate with similar function as the system 500.

The system 600 may include a ground-based processor 610 proximal to a ground-based air traffic control (ATC) facility 612. The ground-based processor 610 may be communicatively coupled to the ATC facility 612 by an ATC interface 614. The ground-based processor 610 may receive sensed operator biometric parameters and operator workspace ambient parameters from multiple vehicles 602 via a data link 360. For example, the data links 360 may be wireless data links connecting each individual vehicle 602 to the ground-based processor 610 via a ground-based relay tower 616 and one or more vehicle interfaces 140. Each set of received operator biometric parameters and operator workspace ambient parameters may be associated with a particular vehicle 602, a particular operator or set of operators, and a particular location or route. A ground-based memory 618 connected to the ground-based processor 610 may store, for example, received operator biometric parameters and received operator workplace ambient parameters along with operator-specific archived biometric data 620, vehicle-specific ambient archived data 622, location-specific and route-specific archived data 624, and vehicle-specific performance data 626.

In operation, the system 600 may analyze received operator biometric parameters and received operator workspace ambient parameters and compare the received parameters with archived data stored in the memory 618 via the ground-based processor 610, determining whether any received biometric or ambient parameters are outside acceptable range and detecting short-term or long-term data patterns associated with a particular operator (not shown) or vehicle 602, a fleet of vehicles, a population of operators, a route or network of routes, a time period, a geographic area, or any combination thereof. The system 600 may respond to identified anomalous parameters or target data patterns by directing a warning device (not shown) of the relevant vehicle 602 to notify an operator or crewmember and (after a delay for operator intervention) directing a vehicle control system (not shown) of the relevant vehicle 602 to adjust a workspace ambient parameter, engaging an autopilot system (not shown) of the relevant vehicle 602, or notifying the ATC facility 612 of the anomalous parameter or target data pattern.

Figure 7:
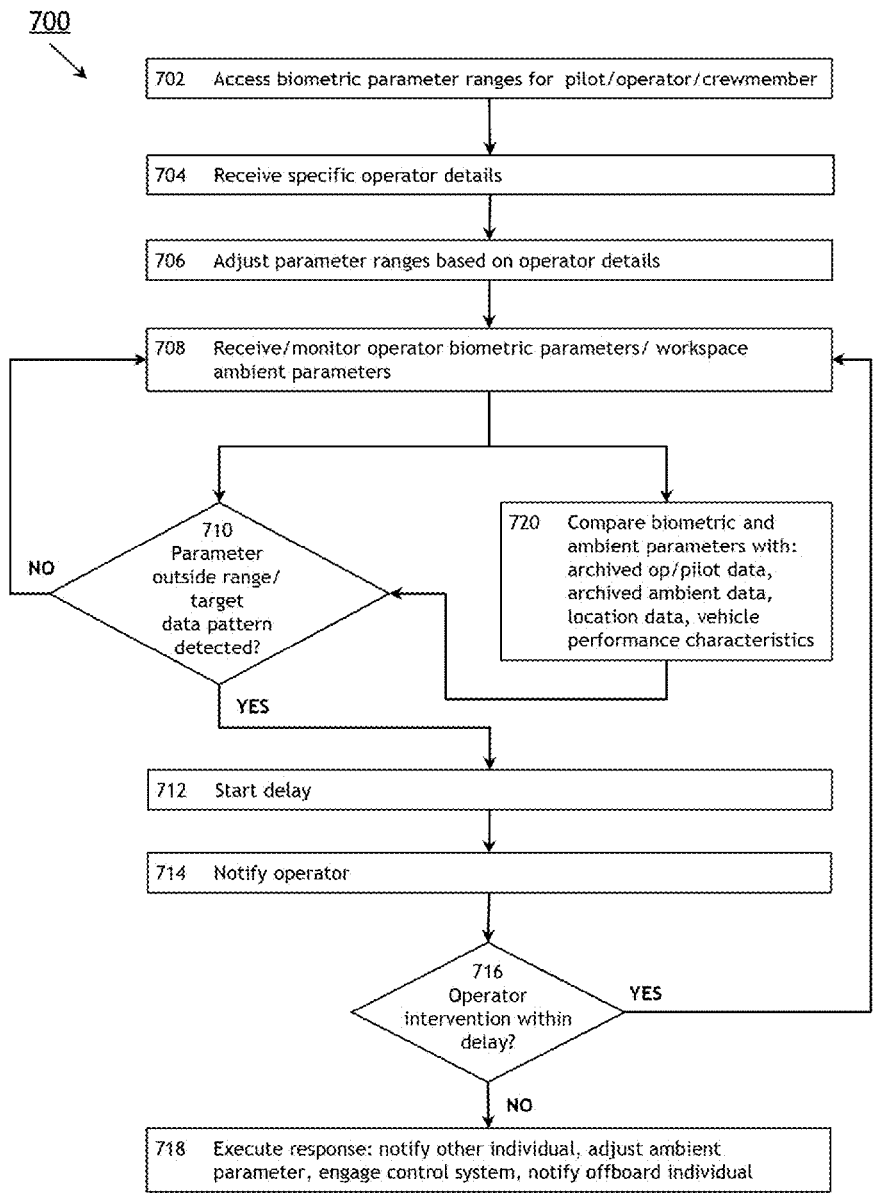
FIG. 7 is a flow diagram of a method for operator capacity monitoring exemplary of one embodiment of the inventive concepts disclosed herein.

Referring to FIG. 7, a flow diagram of a method 700 for operator capacity monitoring exemplary of a biometric embodiment of the inventive concepts disclosed herein is shown. At a step 702, the method 700 may include accessing (ex.—receiving, defining) an acceptable range for an operator biometric parameter via a processor 112 of a PED 110 aboard a vehicle 602. The method 700 may include, at a step 704, receiving (via the processor 112) details associated with a specific operator 102 of the vehicle 602 and, at a step 706, adjusting the parameter acceptable range via the processor 112 based on the received details associated with the operator 102.

At a step 708, the method 700 may receive and monitor the operator biometric parameters (from the operator biometric monitor 504) and the operator workspace ambient parameters (from the workspace ambient monitor 120) via the processor 112. At a step 710, the method 700 may compare (via the processor 112) the received operator biometric parameters and the received operator workspace ambient parameters with stored and adjusted acceptable ranges and determine if parameters are outside acceptable range or if target data patterns are present. If the received parameters are within acceptable ranges and no target data patterns are detected, the method 700 may continue to monitor at the step 708 via the processor 112.

However, if the operator biometric parameters or the workspace operator ambient parameters are outside acceptable ranges, or if target data patterns are detected based on the received operator biometric parameters and received workspace ambient parameters, the method 700 may, at a step 712, activate a variable delay. At a step 714, the method 700 may direct a warning device 282, 284, 286 or an operational display 142 to notify the operator 102 (via the processor 112). At a step 716, the method 700 may determine whether the operator 102 has intervened with or responded to the system 500 within the allotted delay. If the operator 102 has responded, the method 700 may discontinue the warning to the operator 102 and continue to monitor at the step 708 via the processor 112. If the operator 102 has failed to intervene or respond within the allotted delay, the method 700 may, at a step 718, execute a response action via the processor 112 by directing the warning device 282, 284, 286 or the operational display 142 to notify a co-pilot, crewmember, passenger, or other individual aboard the vehicle 602; adjusting an operator workspace ambient parameter of the vehicle 602 via a vehicle control device 170; engaging an autopilot 260 or other control system of the vehicle 602; or sending a notification offboard the vehicle 602.

At a step 720, the method 700 may compare (via the processor 112) the received operator biometric parameters and received operator workspace ambient parameters to archived data associated with the operator 102, archived data associated with the operator workspace ambient parameters, archived data associated with a location or route of the vehicle 602, and data associated with the performance of the vehicle 602. If target data patterns are identified, the method 700 may, at the step 712, activate a variable delay and, at the step 714, notify the operator 102 via the processor 112 depending on the specific nature of the identified target data pattern. If target data patterns are identified, or if the operator 102 fails to provide an expected response within the allotted delay (as determined by the step 716; a response may not always be required), the method 700 may, at the step 718, execute the response action via the processor 112 by directing the warning device 282, 284, 286 or the operational display 142 to notify a co-pilot, crewmember, passenger, or other individual aboard the vehicle 602; directing a vehicle control device 170 to adjust an operator workspace ambient parameter of the vehicle 602; engaging an autopilot 260 or other control system of the vehicle 602; or sending a notification offboard the vehicle 602.

Figure 8:
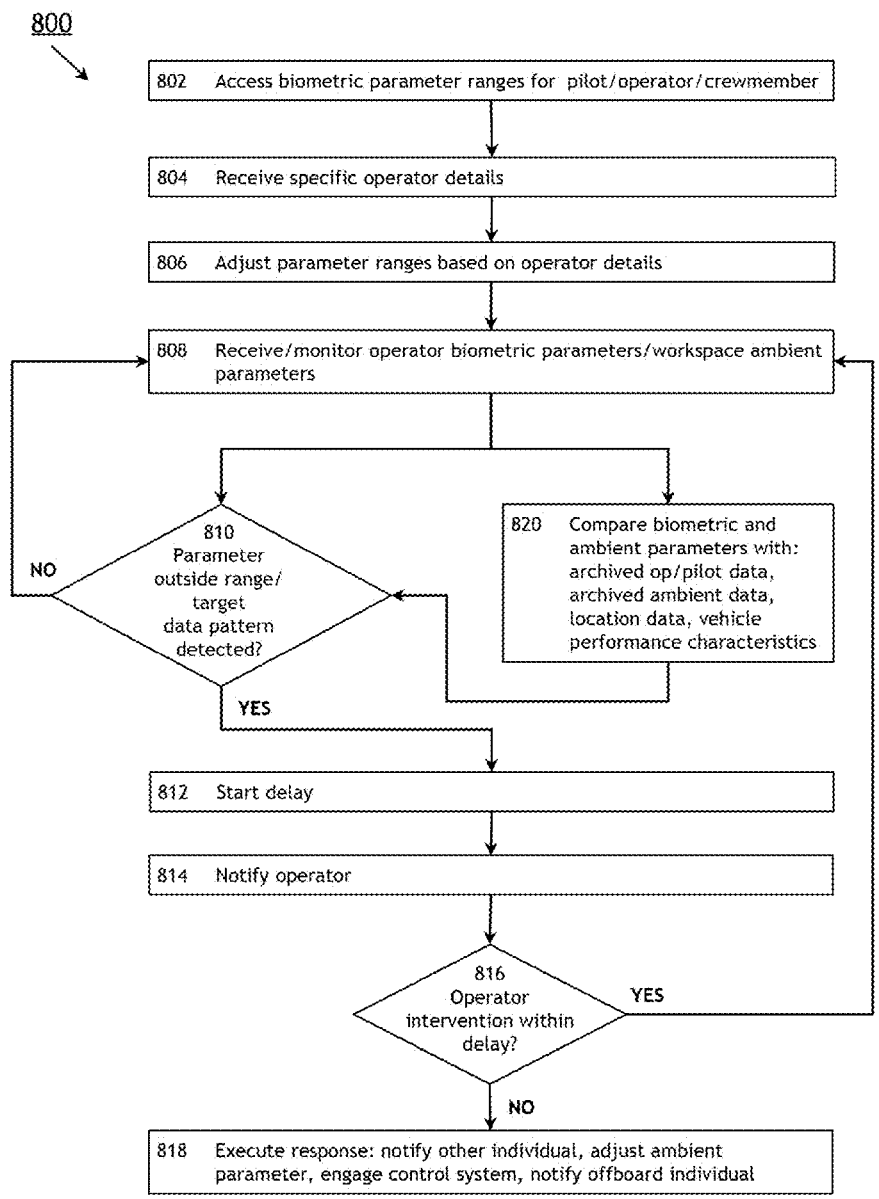
FIG. 8 is a flow diagram of a method for operator capacity monitoring exemplary of one embodiment of the inventive concepts disclosed herein.

Referring to FIG. 8, a flow diagram of a method 800 for operator capacity monitoring exemplary of a multi-vehicle embodiment of the inventive concepts disclosed herein is shown. At a step 802, the method 800 may include accessing (ex.—receiving, defining) an acceptable range for an operator biometric parameter of one or more operators 102 of one or more vehicles 602 via the ground-based processor 610. The method 800 may include, at a step 804, receiving (via the ground-based processor 610) details associated with a specific operator 102 and, at a step 806, adjusting the parameter acceptable range via the ground-based processor 610 based on the received details associated with the specific operator 102.

At a step 808, the method 800 may receive and monitor the operator biometric parameters (from the operator biometric monitor 504) and the operator workspace ambient parameters (from the workspace ambient monitor 120) via the ground-based processor 610. For example, biometric and ambient parameters may be sensed aboard multiple vehicles 602 and forwarded to the ground-based processor 610 via the data link 360 connecting each vehicle 602 to the ground-based processor 610. At the step 810, the method 800 may compare (via the ground-based processor 610) the received operator biometric parameters and the received operator workspace ambient parameters with stored and adjusted acceptable ranges to determine if parameters are outside acceptable ranges for the relevant operator 102 or if target data patterns are present. If received parameters are within acceptable ranges and no target data patterns are detected, the method 800 may continue to monitor at the step 808 via the ground-based processor 610.

However, if the operator biometric parameters or the workspace operator ambient parameters are outside acceptable ranges, or if target data patterns are detected based on the received operator biometric parameters and received workspace ambient parameters, the method 800 may, at a step 812, activate a variable delay and, at a step 814, direct a warning device 282, 284, 286 or an operational display 142 of the relevant vehicle 602 to notify the relevant operator 102 (via the ground-based processor 610 and data link 360 to the vehicle 602). At a step 816, the method 800 may determine (via the ground-based processor 610) whether the operator 102 has intervened with or responded to the system 600 within the allotted delay. If the operator 102 has responded, the method 800 may discontinue the warning to the operator 102 and continue to monitor at the step 808 via the ground-based processor 610. If the operator 102 has failed to intervene or respond within the allotted delay, the method 800 may, at a step 818, execute a response action via the ground-based processor 610 by directing the warning device 282, 284, 286 or the operational display 142 of the relevant vehicle 602 to notify a co-pilot, crewmember, passenger, or other individual aboard the vehicle 602; directing a vehicle control device 170 of the relevant vehicle 602 to adjust an operator workspace ambient parameter of the relevant vehicle 602; engaging an autopilot 260 or other control system of the relevant vehicle 602; or sending a notification to the ATC facility 612.

At a step 820, the method 800 may compare (via the ground-based processor 610) the received operator biometric parameters and received operator workspace ambient parameters to archived data associated with the one or more operators 620, archived data associated with the operator workspace ambient parameters 622, archived data associated with a location or route of the one or more vehicles 624, and data associated with the performance of the one or more vehicles 626. If target data patterns are identified, the method 800 may, at the step 812, activate the variable delay and, at the step 814, direct the warning device 282, 284, 286 or operational display 142 of the relevant vehicle 602 to notify the relevant operator 102 depending on the specific nature of the identified target data pattern. If target data patterns are identified, or if the operator 102 fails to provide an required response within the allotted delay (as determined at the step 816), the method 800 may, at the step 818, execute the response action via the ground-based processor 610 (depending on the specific nature of the identified target data pattern) by directing the warning device 282, 284, 286 or the operational display 142 of the relevant vehicle 602 to notify a co-pilot, crewmember, passenger, or other individual aboard the vehicle 602; directing a vehicle control device 170 of the relevant vehicle 602 to adjust an operator workspace ambient parameter of the relevant vehicle 602;

engaging an autopilot 260 or other control system of the relevant vehicle 602; or sending a notification to the ATC facility 612.

CONCLUSION

Specific blocks, sections, devices, functions, processes, and modules may have been set forth. However, a skilled technologist will realize that there are many ways to partition the system, and that there are many parts, components, processes, modules or functions that may be substituted for those listed above.

Those having skill in the art will recognize that the state of the art has progressed to the point where there may be little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs.

Additionally, implementations of embodiments disclosed herein may include executing a special-purpose instruction sequence or invoking circuitry for enabling, triggering, coordinating, requesting, or otherwise causing one or more occurrences of virtually any functional operations described herein.

While particular aspects of the inventive concepts disclosed herein have been shown and described, it will be apparent to those skilled in the art that, based upon the teachings herein, changes and modifications may be made without departing from the inventive concepts described herein and their broader aspects and, therefore, the appended claims are to encompass within their scope all such changes and modifications as are within the broad scope of the inventive concepts described herein.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently.

We claim:

1. A method for monitoring a capacity of an operator, comprising:
   accessing, via a processor, an acceptable range associated with at least one operator biometric parameter of an operator of a vehicle;
   receiving, via the processor, the at least one operator biometric parameter from at least one operator biometric monitor;
   comparing, via the processor, the received at least one operator biometric parameter with the at least one acceptable range;
   directing, via the processor, at least one warning device of the vehicle to send a first warning to the operator if a result of the comparing includes at least one operator biometric parameter outside the associated acceptable range;
   receiving, via the processor, at least one operator workspace ambient parameter from a workspace ambient monitor;
   identifying, via the processor, at least one target data pattern based on one or more of the at least one operator biometric parameter and the at least one operator workspace ambient parameter;
   directing, via the processor, the at least one warning device to send the first warning to the operator if the at least one target data pattern is identified;
   executing a response action via the processor if either a) the result of the comparing includes the at least one operator biometric parameter outside the associated acceptable range or b) the at least one target data pattern is identified, the execution of the response action after a variable delay and including at least one of:
     1) directing the at least one warning device to send a second warning to at least one of the operator and an individual aboard the vehicle;
     2) directing a vehicle control device to adjust the at least one operator workspace ambient parameter;
     3) activating an autopilot system of the vehicle; and
     4) directing a communications device to send a notification offboard the vehicle; and
   discontinuing the response action based on a receipt of an intervention from the operator during the variable delay.

2. The method of claim 1, wherein the at least one operator biometric parameter includes at least one of a pulse rate, a respiration rate, a skin temperature, an activity level, a perspiration level, a voice stress level, a blood chemical level, and a breath chemical level.

3. The method of claim 1, wherein directing, via the processor, at least one warning device of the vehicle to send a first warning to the operator includes at least one of:
   1) directing, via the processor, at least one audio warning device of the vehicle to send a first auditory warning to the operator;
   2) directing, via the processor, at least one of a visual warning device of the vehicle and an operational display of the vehicle to send a first visual warning to the operator; and
   3) directing, via the processor, at least one physical warning device of the vehicle to send a first tactile warning to the operator.

4. The method of claim 3, wherein the at least one physical warning device includes the at least one operator biometric monitor.

5. The method of claim 1, further comprising:
   acquiring, via the processor, at least one operator specific detail, the at least one operator specific detail acquired via at least one of the at least one operator biometric monitor, an input from the operator, and a memory;
   acquiring, via the processor, an operational status of the vehicle; and
   adjusting, via the processor, the at least one acceptable range based on at least one of the at least one received operator specific detail and the received operational status of the vehicle.

6. The method of claim 1, wherein the at least one operator workspace ambient parameter includes at least one of an air temperature level, a motion level, an air pressure level, a humidity level, a light level, and an air chemical level.

7. The method of claim 1, wherein identifying, via the processor, at least one target data pattern based on one or more of the at least one operator biometric parameter and the at least one operator workspace ambient parameter includes:
   identifying, via the processor, the at least one target data pattern based on one or more of the received at least one operator biometric parameter, the received at least one operator workspace ambient parameter, archived data associated with the at least one operator, archived data associated with the at least one operator workspace ambient parameter, archived data associated with at least one location of the vehicle, and data associated with the performance of the vehicle.

8. A system for monitoring a capacity of an operator, comprising:
- at least one processor;
- a memory operatively connected with the at least one processor, the memory storing non-transitory computer readable program code for monitoring the capacity of an operator of a vehicle, the computer readable program code comprising instructions which, when executed by the at least one processor, cause the at least one processor to perform and direct the steps of:
  - accessing an acceptable range associated with at least one operator biometric parameter of an operator of a vehicle;
  - receiving the at least one operator biometric parameter from at least one operator biometric monitor communicatively coupled to the at least one processor;
  - comparing the received at least one operator biometric parameter with the acceptable range;
  - directing at least one warning device of the vehicle to send a first warning to the operator if a result of the comparing includes at least one operator biometric parameter outside the associated acceptable range;
  - receiving at least one operator workspace ambient parameter from a workspace ambient monitor;
  - identifying at least one target data pattern based on one or more of the at least one operator biometric parameter and the at least one operator workspace ambient parameter;
  - directing the at least one warning device to send the first warning to the operator if the at least one target data pattern is identified;
  - executing a response action if either a) the result of the comparing includes the at least one operator biometric parameter outside the associated acceptable range or b) the at least one target data pattern is identified, the execution of the response action after a variable delay and including at least one of: 1) directing the at least one warning device to send a second warning to at least one of the operator and an individual aboard the vehicle; 2) directing a vehicle control device to adjust the at least one operator workspace ambient parameter; 3) activating an autopilot system of the vehicle; and 4) directing a communications device of the vehicle to send a notification offboard the vehicle; and
  - discontinuing the response action based on a receipt of an intervention from the operator during the variable delay.

9. The system of claim 8, wherein the at least one processor is housed within at least one of a battery powered portable electronic device, a battery powered electronic flight bag, and an aircraft powered and certified electronic flight bag.

10. The system of claim 8, wherein the at least one workspace ambient monitor includes one of a portable battery powered monitor configured to be carried by the operator and a sensor installed in the workspace and receiving power from a vehicle power supply, and wherein the at least one operator workspace ambient parameter includes at least one of an air temperature level, a motion level, an air pressure level, a humidity level, a light level, a volume level, and an air chemical level.

11. The system of claim 8, wherein:
- the at least one operator biometric monitor includes at least one of a monitor worn on a wrist of the operator, a monitor worn on a leg of the operator, a monitor worn on an extremity of the operator, a monitor proximal to a skin of the operator, and a monitor attached to a torso of the operator; and
- the at least one operator biometric parameter includes at least one of a pulse rate, a respiration rate, a skin temperature, an activity level, a perspiration level, a voice stress level, a blood chemical level, and a breath chemical level.

12. The system of claim 8, wherein the instructions further cause the at least one processor to perform and direct the steps of:
- acquiring at least one operator specific detail, the at least one operator specific detail acquired via at least one of the at least one operator biometric monitor, an input from the operator, and a memory;
- acquiring an operational status of the vehicle; and
- adjusting the at least one acceptable range based on at least one of the at least one received operator specific detail and the received operational status of the vehicle.

13. The system of claim 8, wherein the instructions further cause the at least one processor to perform and direct the steps of:
- determining the at least one target data pattern by comparing one or more of the received at least one operator biometric parameter, the received at least one operator workspace ambient parameter, archived data associated with the at least one operator, archived data associated with the at least one operator workspace ambient parameter, archived data associated with at least one location of the vehicle, and data associated with the performance of the vehicle.

* * * * *